United States Patent
Kraemer et al.

(10) Patent No.: US 7,822,581 B2
(45) Date of Patent: Oct. 26, 2010

(54) CAD-SYSTEM FOR DENTAL PROSTHESES

(75) Inventors: Michael A. Kraemer, Landsberg am Lech (DE); Guenter Hertlein, Seefeld (DE); Bernd K. Burger, Alling (DE)

(73) Assignee: 3M Innovative Properties Company, Saint Paul, MN (US)

( * ) Notice: Subject to any disclaimer, the term of this patent is extended or adjusted under 35 U.S.C. 154(b) by 626 days.

(21) Appl. No.: 10/550,993

(22) PCT Filed: Mar. 26, 2004

(86) PCT No.: PCT/EP2004/003259

§ 371 (c)(1),
(2), (4) Date: Sep. 26, 2005

(87) PCT Pub. No.: WO2004/084757

PCT Pub. Date: Oct. 7, 2004

(65) Prior Publication Data

US 2006/0199154 A1    Sep. 7, 2006

(30) Foreign Application Priority Data

Mar. 26, 2003  (DE) .............................. 103 13 691

(51) Int. Cl.
*G06F 17/50* (2006.01)
*G06F 19/00* (2006.01)
(52) U.S. Cl. ...................... 703/1; 700/155; 700/182
(58) Field of Classification Search .................. 703/1; 700/118, 154, 155, 159, 182, 183, 184; 433/29, 433/71, 215, 223

See application file for complete search history.

(56) References Cited

U.S. PATENT DOCUMENTS

| 4,663,720 | A  | * | 5/1987 | Duret et al. ................... 700/163 |
| 6,915,178 | B2 | * | 7/2005 | O'Brien et al. ............. 700/118 |
| 7,236,842 | B2 | * | 6/2007 | Kopelman et al. ........... 700/98 |
| 2001/0001510 | A1 | * | 5/2001 | Rheinberger et al. ......... 264/17 |
| 2002/0013636 | A1 |   | 1/2002 | O'Brien et al. |
| 2002/0102521 | A1 | * | 8/2002 | Iiyama et al. ............... 433/215 |
| 2010/0028836 | A1 | * | 2/2010 | Gubler et al. ............... 433/223 |

FOREIGN PATENT DOCUMENTS

| EP | 1 088 620 A1 | 4/2001 |
| JP | 2001-43260 | 2/2001 |
| JP | 2002-224143 | 8/2002 |
| JP | 2002-304439 | 10/2002 |
| WO | WO 02/085241 A1 | 10/2002 |
| WO | WO 03/007834 A1 | 1/2003 |

OTHER PUBLICATIONS

International Search Report for related PCT/EP2004/003259.

* cited by examiner

*Primary Examiner*—Paul L Rodriguez
*Assistant Examiner*—Andre Pierre Louis

(57) ABSTRACT

The invention relates to a method based on a CAD system consisting of producing a skeleton (14) satisfying pre-defined stability specifications on the basis of a positive template. For this purpose, the control surfaces, which are calculated on the basis of predetermined coordinates of said positive template, are represented on an output device together with the modified surface shape of an implant.

13 Claims, 2 Drawing Sheets

CAD-SYSTEM FOR DENTAL PROSTHESES

BACKGROUND OF THE INVENTION

Figure 1:
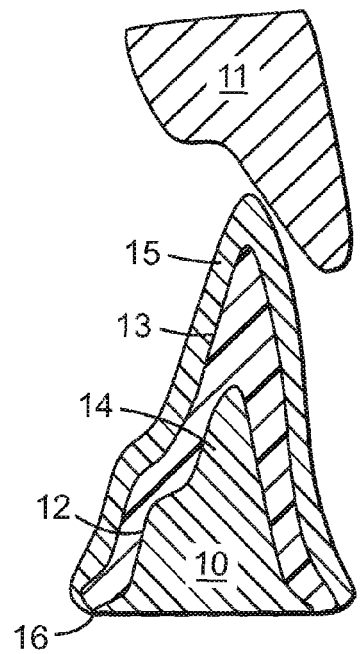

The present invention concerns the production of dental prostheses, more precisely a CAD system for the processing of data for the three-dimensional state of a dental prosthesis.

The term "dental prosthesis" is to be understood here in the broadest sense and should include all types of dental prostheses, such as for example bridges, implants, and dental prostheses in the more narrow sense, but also parts of such dental prostheses, like for example crowns structures and bridge structures, onto which a veneer still has to be applied to obtain a finished crown or bridge, as well as individual bridge structures or bridge units.

The invention therefore comprises not only two-unit bridge structures for example, in which the two units are connected by connection arms, but also three or multi-unit bridge structures, whereby a connection arm connects each of the two neighboring units. The units can be anchors, intermediate units, or free terminal units as needed: an anchor is like a crown mounted on a tooth stump serving as abutment pillar, an intermediate unit is between two units and not mounted to an abutment pillar, and a free terminal unit is only attached to a unit and not to an abutment pillar. The invention also comprises these units.

DESCRIPTION OF THE STATE-OF-THE-ART

It is known that the data of the three-dimensional shape of crown and bridge structures can be processed with the help of a CAD system, which is part of a CIM system available by the name LAVA offered by 3M ESPE AG (Seefeld, Germany) for the production of ceramic crown and bridge structures.

The CAD system is connected on the one hand to an optical scanner in this known LAVA system, and on the other hand to an NC milling machine. The scanner detects the three-dimensional surface of a dental impression and transfers the scanned data to the CAD system. These surface data can be processed and modified with this CAD system as desired by the user to design the three-dimensional shape of the crown or bridge structure, and the resulting data of the shape are then sent to the NC milling machine. The NC milling machine finally machines a ceramic blank of zirconia or zirconium dioxide in mostly precise agreement with the design data.

The crown structures designed with this known CAD system feature a uniform thickness. The corresponding design data for the structure are calculated as follows automatically by the system from the input data of the scanner, which represent the three-dimensional surface of the tooth stump prepared for the crown: the input data of the surface are copied, and these copied data are then scaled outward relative to the source data such that the normal distance for each point on the original surface, hence, the distance in the direction of the vector normal to the surface, assumes a predetermined fixed value to the outer surface of the copy. This fixed value therefore represents the uniform thickness of the structure and is chosen such that the structure obtains the desired stability required to withstand the loads from the milling work later on, and from chewing after completing the fabrication and mounting to the tooth stump.

These crown structures of uniform thickness designed with the known CAD system are in general very useful, but lead to problems in special cases as explained in more detail in the following in examples by use of FIG. 2.

Figure 2:
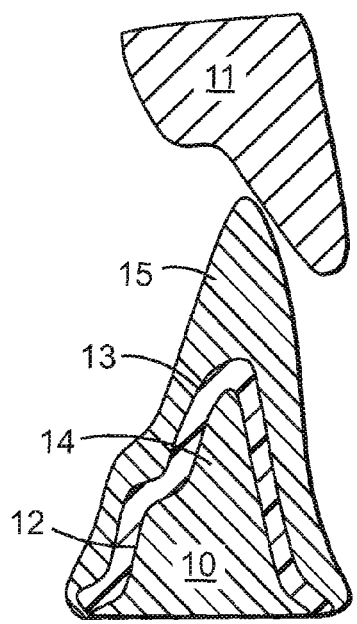

Shown in cross section in FIG. 2 are a lower incisor tooth, more precisely its stump 10 prepared up to the preparation border 16, and the upper opposing tooth 11. The dentist had to remove the incisor part of the lower tooth to a great extent in the shown problematic case so that now a large gap exists between the tooth stump 10 and opposing tooth 11. The scaled data of the replica for the outer structure surface 13 are now calculated with the known CAD system starting from the original data of the stump surface 12 above the preparation border 16, which are positioned at a uniform distance to the stump surface 12 so that the structure 14 features a uniform thickness.

As can be easily seen from FIG. 2, the veneering 15 applied by the dental technician to the structure 14 has to close the remaining gap to the opposing tooth 11, which is hardly closed by structure 14. The thickness of the veneering should however not exceed a certain maximum value since otherwise the stability of the veneering is reduced too much.

DESCRIPTION OF THE INVENTION

The invention suggests an intervention for this problem with a first aspect by suggesting that the structure in the incisal area be designed thicker than typical up to this point. This can be easily seen from FIG. 1.

This can be achieved by a so-called "global" modification of the known outer structure surface 13', for example, which belongs to the uniform thickness of the structure 14', by scaling the surfaces of the replica calculated in known manner differently in at least two spatial axes. The surface of the replica representing the outer structure surface 13 of the structure 14 shown in FIG. 1 was more strongly increased in vertical direction for example than in sagittal direction.

The veneering 15 of FIG. 1 in the incisor region is significantly thinner as a result than the veneering 15' of FIG. 2 so that a higher stability is obtained. Moreover, the dental technician can produce the veneering 15 of FIG. 1 quicker since less material has to be applied to structure 14.

The global modification according to the invention can be performed by the CAD systems such that the lower preparation border 16 is not changed. This is important for a precise seating of the structure 14 on stump 10. Moreover, the scaling in a specific spatial axis can be performed not only with a constant scaling factor, but also with a variable scaling factor that depends on the distance from the preparation border 16, for example. Thus, a trapezoidal scaling function can be used for the vertical axis and/or the sagittal axis, for example so that the replica or structure surface 13 are distorted the most in the incisal area. This way, the natural shape of the tooth can be most closely approximated.

It is also possible to choose the scaling for the positive and the negative part of a spatial axis different to thereby achieve a different distortion in distal direction than in mesial direction, for example.

Inputting data via keyboard and/or with a mouse can set the scaling.

Since a global modification cannot cover all possible optimal cases, the invention provides in a second aspect a so-called "local" modification. This can mimic a conventional wax knife, for example, to ease the application for the dental technician.

Figure 3:
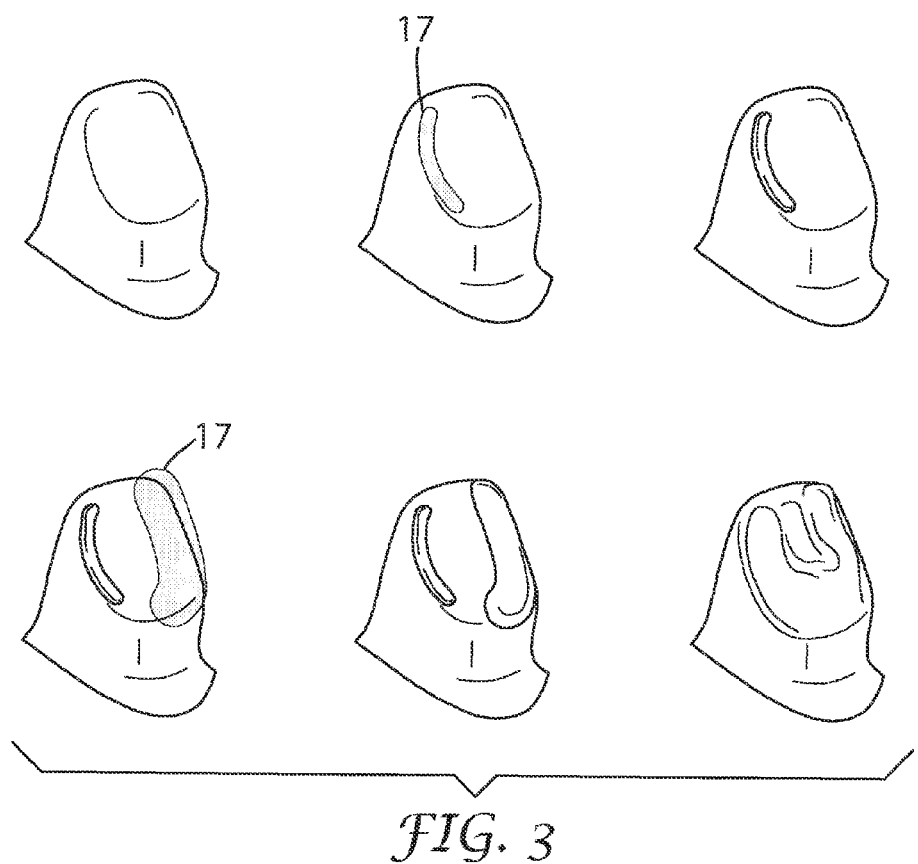

As shown in the image series of FIG. 3, the practitioner has to mark the areas of the surface with the mouse (shown in red in FIG. 3), which then have to be modified with the previously set parameters. These parameters comprise at least the diameter and the thickness of the local modification. The term thickness describes here the thickness of the applied or removed structure material. A so-called temperature can also be used, which defines how much the surface should be smoothened during the modification.

Certain conditions have to be fulfilled for any modification to ensure minimum stability requirements of the prostheses are met. For example, a structure has to have a minimum wall thickness to avoid breakage. This can be controlled according to a third aspect of the present invention by creating an additional control surface, which meets the minimal stability requirements and is shown together with the actual surface of the structure.

The invention relates in a fourth aspect to a method for the processing of data of the three-dimensional shape of a dental prosthesis (14), featuring the following steps:
a) input data are provided representing the three-dimensional surface of the stump (10) prepared for the prosthesis (14);
b) minimum stability requirements are provided for the prosthesis (14);
c) control data are generated from the input data, which show the control surface, and which meet the minimum stability requirements;
d) data of the shape are created showing the three-dimensional shape of the prosthesis (14);
e) the shape of the prosthesis (14) is shown together with the control surface.

The input data in step a) can be provided by a scanner, which detects the three-dimensional surface of a dental impression, or by an intra-oral scanner, which captures the three-dimensional surface of the dental situation in the mouth of the patient.

The stability requirements in step b) can be provided automatically for example with the help of a computer, and/or manually by the user.

The control data in step c) can be generated automatically for example with the help of a computer, and/or manually by the user.

The shape data in step d) can be generated automatically for example with the help of a computer, and/or manually by the user.

The representation in step e) can be accomplished with the help of the monitor.

The sequence of steps can be chosen as desired or needed. For example, step d) can be performed before, at the same time, or after step c). Also, the control surface by itself can be shown first in step e), for example, and then additionally the shape of the prosthesis, for example by super exposure, but a reverse sequence or a simultaneous start of the imaging is also possible.

It can be provided that this method features the following additional steps:
f) the shape data are modified;
g) the actual shape of the prosthesis (14), which represents the modified shape data, is shown together with the control surface.

The shape data can be modified globally in step f), for example according to the above-given definition, and/or locally, for example, according to the above-given definition, and/or automatically, for example with the help of a computer, and/or manually by the user.

The control surface can be shown first by itself in step g), for example, followed then by the actual shape of the prosthesis, for example by super exposure, but a reverse sequence or the simultaneous start of the imaging is also possible.

It can be provided that the shape data in step d) are generated from the input data.

It can be provided that the shape data are modified globally such that a given preparation edge (16) remains unchanged.

It can be provided that the control surface exactly meets the minimum stability requirements.

It can be provided that the method according to the invention is performed with the help of a computer program.

The present invention relates in a fifth aspect to a data processing system for performing the method according to the invention with:
an input device for the data required for the method;
a central processing unit connected to the input device, in which the program runs for processing the data according to the method;
an output device connected to the central processing unit for the shape of the prosthesis (14) and the control surface.

The present invention relates in a sixth aspect to a computer program designed to perform the method according to the invention.

The present invention relates in a seventh aspect to a computer program that performs the method according to the invention when it is run on the computer.

The present invention relates in an eighth aspect to a computer program featuring commands that perform the method according to the invention.

The present invention relates in a ninth aspect to a computer program that implements the method according to the invention.

The present invention relates in a tenth aspect to a data storage device, which stores the computer program according to the invention. The data storage device can be a floppy disc, a magnetic tape, a CD, a DVD, a memory stick, a hard drive, a RAM component, or a ROM component, for example.

The present invention has now been described referencing different types of its embodiments. It becomes clear to the expert that many changes can be performed on the described embodiments without deviating from the scope of the present invention. The scope of the present invention shall therefore not be limited to the structures described in this application, but only by the structures described by the verbiage of the claims as well as equivalents of those structures.

List of References

10 Stump
11 Opposing tooth
12 Stump surface
13, 13' Outer structure surface
14, 14' Stucture
15, 15' Veneering
16 Preparation edge

The invention claimed is:

1. A method for processing data regarding a dental prosthesis, the method comprising the steps of:
a) providing input data which represent a three-dimensional surface of a tooth stump prepared for a prosthesis;
b) providing stability requirements for the prosthesis, wherein the stability requirements include a minimum required thickness of the prosthesis,
c) generating control data from said input data, said control data representing a control surface which meets the stability requirements,
d) generating design data from said input data and separately from the control data which represent the three-dimensional shape of the prosthesis, and
e) displaying the shape of the prosthesis together with the control surface on a monitor;
wherein the displayed control surface provides a visual representation of the minimum required thickness, the design data are modified by a user based on a visual comparison of the displayed design data and the displayed control surface in order to meet the stability requirements; and the design of the prosthesis corresponding to the modified design data is displayed on the monitor together with the control surface.

2. The method according to claim 1, wherein an outer surface of the prosthesis is scaled differently in at least two spatial axes such that a given preparation margin remains thereby unchanged.

3. The method according to claim 1, wherein the control surface meets the minimum stability requirements for the prosthesis.

4. The method according to claim 1, wherein the input data is provided by a scanner.

5. The method according to claim 4, wherein the scanner is an intra-oral scanner.

6. The method according to claim 2, wherein the outer surface of the prosthesis is scaled based on data input via a keyboard.

7. The method according to claim 1, wherein an outer surface of the prosthesis is scaled in at least two spatial axes, and wherein at least one spatial axis has a variable scaling factor.

8. The method according to claim 1, wherein the stability requirements are automatically provided by a computing apparatus.

9. The method according to claim 1, wherein the control data are generated automatically by a computing apparatus.

10. A data processing system comprising:
   a) an input device for data regarding a three dimensional surface of a tooth stump prepared for a dental prosthesis;
   b) a central unit connected to the input device and running a program for processing the data according to a method comprising the steps of:
      i) providing input data which represent a three-dimensional surface of a tooth stump prepared for a prosthesis,
      ii) providing stability requirements for the prosthesis, wherein the stability requirements include a minimum required thickness of the prosthesis,
      iii) generating control data from said input data, said control data representing a control surface which meets the stability requirements,
      iv) generating design data from said input data and separately from the control data which represent the three-dimensional shape of the prosthesis, and
      v) displaying the shape of the prosthesis together with the control surface on a monitor;

wherein the displayed control surface provides a visual representation of the minimum required thickness, the design data are modified by a user based on a visual comparison of the displayed design data and the displayed control surface in order to meet the stability requirements; and the design of the prosthesis corresponding to the modified design data is displayed on the monitor together with the control surface; and c) a display device connected to the central unit for the design of the prosthesis and the control surface.

11. The data processing system according to claim 10, wherein the stability requirements are automatically provided by the central unit.

12. The data processing system according to claim 10, wherein the control data are generated automatically by the central unit.

13. A method for processing data regarding a dental prosthesis, the method comprising the steps of:
   a) providing input data, by means of an intra-oral scanner, which represent a three-dimensional surface of a tooth stump prepared for a prosthesis;
   b) providing stability requirements for the prosthesis, wherein the stability requirements include a minimum required thickness of the prosthesis,
   c) generating control data from said input data, said control data representing a control surface which meets the stability requirements for the prosthesis, wherein control data are generated automatically by a computing apparatus,
   d) generating design data from said input data and separately from the control data which represent the three-dimensional shape of the prosthesis,
   e) scaling an outer surface of the prosthesis in at least two spatial axes, wherein at least one spatial axis has a variable scaling factor, and
   f) displaying the shape of the prosthesis together with the control surface on a monitor;

wherein the displayed control surface provides a visual representation of the minimum required thickness, the design data are modified by a user based on a visual comparison of the displayed design data and the displayed control surface in order to meet the stability requirements; and the design of the prosthesis corresponding to the modified design data is displayed on the monitor together with the control surface.

* * * * *